(12) United States Patent
Choi et al.

(10) Patent No.: US 11,352,608 B2
(45) Date of Patent: Jun. 7, 2022

(54) PROMOTER AND A METHOD FOR PRODUCING L-AMINO ACID USING THE SAME

(71) Applicant: CJ CHEILJEDANG CORPORATION, Seoul (KR)

(72) Inventors: Sun Hyoung Choi, Seoul (KR); Jin Sook Chang, Suwon-si (KR); Hyung Joon Kim, Seoul (KR); Byoung Hoon Yoon, Seoul (KR); Ji Yeon Lee, Suwon-si (KR); Yunjung Choi, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/466,940

(22) PCT Filed: Mar. 8, 2019

(86) PCT No.: PCT/KR2019/002708
§ 371 (c)(1),
(2) Date: Jun. 5, 2019

(87) PCT Pub. No.: WO2019/172702
PCT Pub. Date: Sep. 12, 2019

(65) Prior Publication Data
US 2021/0002654 A1   Jan. 7, 2021

(30) Foreign Application Priority Data
Mar. 9, 2018 (KR) .................. 10-2018-0028184

(51) Int. Cl.
| | |
|---|---|
| *C12N 9/04* | (2006.01) |
| *C12N 7/00* | (2006.01) |
| *C12N 15/00* | (2006.01) |
| *C12N 1/20* | (2006.01) |
| *C12N 15/77* | (2006.01) |
| *C12P 7/00* | (2006.01) |
| *C12P 13/14* | (2006.01) |

(52) U.S. Cl.
CPC .......... *C12N 9/0006* (2013.01); *C12N 15/77* (2013.01); *C12P 7/00* (2013.01); *C12Y 101/01027* (2013.01); *C12P 13/14* (2013.01)

(58) Field of Classification Search
CPC .............. C12N 9/0006; C12N 15/1137; C12N 9/006; C12P 7/00
See application file for complete search history.

(56) References Cited

U.S. PATENT DOCUMENTS

| | | |
|---|---|---|
| 3,220,929 A | 11/1965 | Kinoshita et al. |
| 6,682,912 B2 | 1/2004 | Moriya et al. |
| 7,141,388 B2 | 11/2006 | Crafton et al. |

FOREIGN PATENT DOCUMENTS

| | | |
|---|---|---|
| CN | 107012160 A | 8/2017 |
| KR | 10-0292299 B1 | 6/2001 |
| KR | 10-0924065 B1 | 10/2009 |
| KR | 10-2015-0042692 A | 4/2015 |
| WO | 2008/033001 A1 | 3/2008 |
| WO | 2015/005406 A1 | 1/2015 |

OTHER PUBLICATIONS

Inui. AB191244. GenBank. Jul. 22, 2009.*
Toyoda et al., The ldhA Gene, Encoding Fermentative $_L$-Lactate Dehydrogenase of *Corynebacterium glutamicum*, Is under the Control of Positive Feedback Regulation Mediated by LldR, *Journal of Bacteriology* 191(13):4251-4258 (Jul. 2009).
Genbank Accession No. AB191244 (Jul. 22, 2009) (20 pages).
Toyoda et al., "Molecular mechanism of SugR-mediated sugar-dependent expression of the ldhA gene encoding $_L$-lactate dehydrogenase in *Corynebacterium glutamicum*," *Appl Microbiol Biotechnol* 83:315-327 (2009).

* cited by examiner

*Primary Examiner* — Yong D Pak
(74) *Attorney, Agent, or Firm* — Seed IP Law Group LLP

(57) ABSTRACT

The present disclosure relates to a novel promoter and a method for producing L-amino acids using the promoter, and more specifically, to a novel polynucleotide having promoter activity, a vector and a microorganism of the genus *Corynebacterium* comprising the polynucleotide, a method for producing L-amino acids using the microorganism, and a fermented composition.

12 Claims, No Drawings
Specification includes a Sequence Listing.

SEQUENCE LISTING

```
<160> NUMBER OF SEQ ID NOS: 9

<210> SEQ ID NO 1
<211> LENGTH: 44
<212> TYPE: DNA
<213> ORGANISM: Artificial Sequence
<220> FEATURE:
<223> OTHER INFORMATION: LDH promoter region

<400> SEQUENCE: 1
tggtctgacc acattttcgg acataatcgg gcataagtaa aggt            44

<210> SEQ ID NO 2
<211> LENGTH: 44
<212> TYPE: DNA
```

<213> ORGANISM: Corynebacterium glutamicum

<400> SEQUENCE: 2
tggtctgacc acattttcgg acataatcgg gcataattaa aggt        44

<210> SEQ ID NO 3
<211> LENGTH: 945
<212> TYPE: DNA
<213> ORGANISM: Corynebacterium glutamicum

<400> SEQUENCE: 3

```
atgaaagaaa ccgtcggtaa caagattgtc ctcattggcg caggcgatgt cggagttgca      60
tacgcatatg cactgatcaa ccaaggcatg gcagaccacc ttgcgatcat cgacattgat     120
gaaaagaaac tcgaaggcaa cgtcaaggac ttaaaccatg gtgttgtgtg ggccgattcc     180
cgcacccgcg tcactaaggg aacctacgct gactgcgaag acgcagccat ggttgtcatt     240
tgtgccggcg cagcccaaaa gccaggcgag acccgcctcc agctggtgga caaaaacgtc     300
aagattatga atccatcgt cggcgatgtc atggacagcg gattcgacgg catcttcctc     360
gtggcgtcca acccagtgga tatcctgacc tacgcagtgt ggaaattctc cggcttggaa     420
tggaaccgcg tgatcggctc cggaactgtc ctggactccg ctagattccg ctacatgctc     480
ggcgaactct atgaagtggc accaagctcc gtccacgcct acatcatcgg cgaacacgga     540
gacaccgaac ttccagtcct gtcctccgcg accatcgccg cgtatcgct tagccgaatg     600
ctggacaaag acccagagct tgagggccgt ctagagaaaa ttttcgaaga cacccgcgac     660
gctgcctatc acattatcga cgccaagggc tccacttcct acggcatcgg catgggtctt     720
gctcgcatca cccgcgcaat cctacaaaac caagacgttg cagtcccagt ctctgcactg     780
ctccacggtg aatacggtga ggaagacatc tacatcggca ccccagctgt ggtgaaccgc     840
cgaggcatcc gccgcgttgt cgaactagaa atcaccgacc acgagatgga acgcttcaag     900
cattccgcaa ataccctgcg cgaaattcag aagcagttct tctaa                     945
```

<210> SEQ ID NO 4
<211> LENGTH: 314
<212> TYPE: PRT
<213> ORGANISM: Corynebacterium glutamicum

<400> SEQUENCE: 4

```
Met Lys Glu Thr Val Gly Asn Lys Ile Val Leu Ile Gly Ala Gly Asp
1               5                   10                  15

Val Gly Val Ala Tyr Ala Tyr Ala Leu Ile Asn Gln Gly Met Ala Asp
            20                  25                  30

His Leu Ala Ile Ile Asp Ile Asp Glu Lys Lys Leu Glu Gly Asn Val
        35                  40                  45

Lys Asp Leu Asn His Gly Val Val Trp Ala Asp Ser Arg Thr Arg Val
    50                  55                  60

Thr Lys Gly Thr Tyr Ala Asp Cys Glu Asp Ala Ala Met Val Val Ile
65                  70                  75                  80

Cys Ala Gly Ala Ala Gln Lys Pro Gly Glu Thr Arg Leu Gln Leu Val
                85                  90                  95

Asp Lys Asn Val Lys Ile Met Lys Ser Ile Val Gly Asp Val Met Asp
            100                 105                 110

Ser Gly Phe Asp Gly Ile Phe Leu Val Ala Ser Asn Pro Val Asp Ile
        115                 120                 125
```

Leu Thr Tyr Ala Val Trp Lys Phe Ser Gly Leu Glu Trp Asn Arg Val
    130                 135                 140

Ile Gly Ser Gly Thr Val Leu Asp Ser Ala Arg Phe Arg Tyr Met Leu
145                 150                 155                 160

Gly Glu Leu Tyr Glu Val Ala Pro Ser Ser Val His Ala Tyr Ile Ile
                165                 170                 175

Gly Glu His Gly Asp Thr Glu Leu Pro Val Leu Ser Ser Ala Thr Ile
            180                 185                 190

Ala Gly Val Ser Leu Ser Arg Met Leu Asp Lys Asp Pro Glu Leu Glu
        195                 200                 205

Gly Arg Leu Glu Lys Ile Phe Glu Asp Thr Arg Asp Ala Ala Tyr His
    210                 215                 220

Ile Ile Asp Ala Lys Gly Ser Thr Ser Tyr Gly Ile Gly Met Gly Leu
225                 230                 235                 240

Ala Arg Ile Thr Arg Ala Ile Leu Gln Asn Gln Asp Val Ala Val Pro
                245                 250                 255

Val Ser Ala Leu Leu His Gly Glu Tyr Gly Glu Glu Asp Ile Tyr Ile
            260                 265                 270

Gly Thr Pro Ala Val Val Asn Arg Arg Gly Ile Arg Arg Val Val Glu
        275                 280                 285

Leu Glu Ile Thr Asp His Glu Met Glu Arg Phe Lys His Ser Ala Asn
    290                 295                 300

Thr Leu Arg Glu Ile Gln Lys Gln Phe Phe
305                 310

<210> SEQ ID NO 5
<211> LENGTH: 75
<212> TYPE: DNA
<213> ORGANISM: Artificial Sequence
<220> FEATURE:
<223> OTHER INFORMATION: Synthetic oligonucleotide

<400> SEQUENCE: 5
caagagcttg tgcccggatt cctttgttac acctttactt atgcccgatt atgtccgaaa    60
atgtggtcag accaa    75

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
cggtacccgg ggatcctgtg ggtggcgttg ta    32

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
ctttgttaca cctttactta tgcccgatta tgt    33

<210> SEQ ID NO 8
<211> LENGTH: 33
<212> TYPE: DNA

```
<213> ORGANISM: Artificial Sequence
<220> FEATURE:
<223> OTHER INFORMATION: Primer

<400> SEQUENCE: 8
gtaaaggtgt aacaaaggaa tccgggcaca agc                                    33

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
atgcctgcag gtcgacccac actgcgtagg tc                                     32
```

PROMOTER AND A METHOD FOR PRODUCING L-AMINO ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_445USPC_SEQUENCE_LISTING.txt. The text file is 5.3 KB, was created on May 23, 2019, and is being submitted electronically via EFS-Web.

TECHNICAL FIELD

The present disclosure relates to a novel promoter and a method for producing L-amino acid using the promoter, and more specifically, to a novel polynucleotide having promoter activity, a vector and a microorganism of the genus *Corynebacterium* comprising the polynucleotide, a method for producing L-amino acids using the microorganism, and a fermented composition

BACKGROUND ART

L-Glutamic acid is a representative amino acid produced by fermentation and has a unique, distinctive taste, and thus is an important amino acid widely used in the food field as well as in the medical field and other animal feed fields.

It is known that a typical method for producing L-glutamic acid includes a fermentation method using a microorganism of the genus *Brevibacterium* or *Corynebacterium* and a coryneform bacterium including a mutant strain thereof (Amino Acid Fermentation, Gakkai Shuppan Center: 195-215, 1986) or using *Escherichia coli* or microorganisms of the genera *Bacillus, Streptomyces, Penicillum, Klebsiella, Envinia, Pantoea*, etc. (U.S. Pat. Nos. 3,220,929 and 6,682, 912). When L-glutamic acid is produced through microbial fermentation, various materials in addition to L-glutamic acid, including organic acids, are mixed in a fermented product.

These organic acids are acidic organic compounds, and include lactic acid, acetic acid, formic acid, citric acid, oxalic acid, uric acid, etc. Organic acids in foods exhibit sour and umami tastes, and have the effect of preventing decay by lowering the pH of the foods. It is generally known that lactic acid accounts for the largest portion of organic acids produced through microbial fermentation.

However, as the portion of lactic acids produced by fermentation is higher, the sour taste in the fermented produced increases, and as a result, the palatability may be decreased. Therefore, it is necessary to regulate the production amount of lactic acid in the fermented product produced through microbial fermentation.

With this background, the present inventors have made efforts to reduce the organic acid productivity in a microorganism producing L-glutamic acid. As a result, the present inventors have developed a novel polynucleotide having the promoter activity of the present disclosure, and discovered that the polynucleotide can increase the L-glutamic acid productivity in the strain and that it can reduce the lactic acid productivity, thereby completing the present disclosure.

DISCLOSURE

Technical Problem

An objective of the present disclosure is to provide a polynucleotide having promoter activity, wherein the $37^{th}$ nucleotide of the nucleotide sequence of SEQ ID NO: 2 is substituted with G.

Another objective of the present disclosure is to provide a vector comprising the polynucleotide; and a gene encoding a target protein operably linked to the polynucleotide.

Still another objective of the present disclosure is to provide a microorganism of the genus *Corynebacterium* comprising the polynucleotide; and a gene encoding a target protein operably linked to the polynucleotide.

Still another objective of the present disclosure is to provide a method for producing a target substance, comprising: culturing the microorganism of the genus *Corynebacterium* in a medium; and recovering a target substance from the medium.

Still another objective of the present disclosure is to provide a method for preparing a fermented composition, comprising fermenting by culturing the microorganism of the genus *Corynebacterium* in a medium.

Still another objective of the present disclosure is to provide a fermented composition prepared by the above method.

Technical Solution

Hereinbelow, the present disclosure will be described in detail. Meanwhile, each description and embodiment disclosed in the present disclosure may be applied to other descriptions and embodiments. That is, all combinations of various elements disclosed in the present disclosure fall within the scope of the present disclosure. Further, the specific descriptions disclosed below should not be construed as limiting the scope of the present disclosure.

To achieve the objectives above, an aspect of the present disclosure provides a polynucleotide having promoter activity, wherein the $37^{th}$ nucleotide of the nucleotide sequence of SEQ ID NO: 2 is substituted with G.

As used herein, the term "nucleotide sequence of SEQ ID NO: 2" may refer to a part of the promoter sequence of a gene encoding lactate dehydrogenase (LDH).

In particular, the term "lactate dehydrogenase" refers to an enzyme that produces lactate, i.e., lactic acid, using pyruvate as a substrate, and may interchangeably be named as "LDH" in the present disclosure. Specifically, the gene of lactate dehydrogenase may include the nucleotide sequence of SEQ ID NO: 3, and the protein thereof may include the amino acid sequence of SEQ ID NO: 4, but these are not limited thereto.

As used herein, the term "promoter" refers to a sequence of a non-translated nucleotide upstream of a coding region, which includes a polymerase-binding domain and has a transcription initiation activity for a target gene of the promoter into mRNA, that is, a DNA domain to which a polymerase binds to initiate the transcription of a gene, and may be located at the 5'-region of the initiation area of mRNA transcription. In particular, the target gene of the promoter may be lactate dehydrogenase, but is not limited thereto.

The polynucleotide of the present disclosure is one in which the nucleotide sequence of SEQ ID NO: 2, i.e., the promoter sequence of the gene of lactate dehydrogenase, is mutated. Specifically, the mutation may be a substitution of T, which is the 37$^{th}$ nucleotide of the sequence above, with G. Accordingly, the polynucleotide may consist of the nucleotide sequence of SEQ ID NO: 1.

In particular, the term "modification" refers to a phenotypic change that is genetically or non-genetically stable, and may be interchangeably referred to as "mutation" in the present disclosure.

Specifically, the polynucleotide may have promoter activity that is modified (increased or decreased) relative to the activity of a polynucleotide, which does not include the polynucleotide modification. Accordingly, the expression of a target gene operably linked to the polynucleotide and the activity of a protein encoded by the target gene may be regulated (increased or decreased), and further, the expression of genes other than the target gene may be regulated.

For the objectives of the present disclosure, the polynucleotide may be one for attenuating the activity of lactate dehydrogenase.

Additionally, the polynucleotide may be one for increasing the production amount of L-glutamic acid and/or for decreasing the production amount of lactic acid.

It has been known that lactate dehydrogenase is involved in the production of lactic acid, but the relationship thereof with the production of L-glutamic acid is not known and was first identified by the present inventors. In particular, the present inventors have confirmed for the first time the decrease in the activity of lactate dehydrogenase by the modification of the promoter of lactate dehydrogenase, as well as the effects of increasing the production amount of L-glutamic acid and decreasing the production amount of lactic acid due to the same.

Herein, "L-glutamic acid" or "L-glutamate" refers to a kind of amino acid and is classified as a non-essential amino acid. L-Glutamic acid is known to be the most common excitatory neurotransmitter in the central nervous system. In addition, since L-glutamic acid has an umami taste, monosodium glutamate (MSG) has been developed therefrom and is widely used as a flavor enhancer. It is generally produced through fermentation of microorganisms producing L-glutamic acid.

Additionally, the term "lactic acid" is a kind of organic acid having a sour taste. In addition, lactic acid is used as a sour taste agent for fruit extracts, syrups, and soft drinks for edible purposes, and is used to prevent the propagation of saprogenic bacteria at the early stages of fermentation of alcohols. Lactic acid is generally produced by fermentation in microorganisms producing lactic acid. In addition, if overproduced, the quality of the fermented product may deteriorate due to an excessively sour taste, and thus the concentration of lactic acid needs to be appropriately regulated during the culture.

Specifically, the polynucleotide may be one composed of the nucleotide sequence of SEQ ID NO: 1.

Additionally, the nucleotide sequence of the present disclosure may be modified by known mutagenesis methods, such as directed evolution, site-directed mutagenesis, etc.

Therefore, the polynucleotide may comprise a polynucleotide including the nucleotide sequence that has a homology to the nucleotide sequence of SEQ ID NO: 1 of at least 60%, specifically at least 70%, more specifically at least 80%, and even more specifically at least 83%, 84%, 88%, 90%, 93%, 95%, or 97%. It is apparent that a polynucleotide sequence having such homology, a part of which is deleted, modified, substituted, or added, is also within the scope of the present disclosure, as long as the resulting polynucleotide sequence has a biological activity substantially equivalent or corresponding to the nucleotide sequence of SEQ ID NO: 1.

As used herein, the term "homology" may indicate the degree of matching with the given nucleotide sequence, and may be presented as a percentage (%). In the present disclosure, a homology sequence having an activity which is identical or similar to the given nucleotide sequence is presented as "% homology". The homology to the nucleotide sequence can be determined by, for example, algorithm BLAST (see Karlin and Altschul, Pro. Natl. Acad. Sci. USA, 90, 5873(1993) or FASTA (see Pearson, Methods Enzymol., 183, 63, 1990). Based on this algorithm, programs called BLASTN or BLASTX have been developed (see http://www.ncbi.nlm.nih.gov).

As used herein, the term "stringent conditions" refers to conditions which permit specific hybridization between polynucleotides. For example, such stringent conditions are specifically described in the literature (e.g., J. Sambrook et al.). For example, the stringent conditions may include conditions in which genes having a high homology (e.g., 60% or more, specifically 90% or more, more specifically 95% or more, even more specifically 97% or more, and even more specifically 99% or more) can hybridize with each other, whereas genes having a lower homology thereof cannot hybridize with each other; or conditions for conventional southern hybridization (i.e., conditions for washing once, and specifically two or three times at a salt concentration and temperature corresponding to 60° C., 1×SSC, 0.1% SDS, specifically at 60° C., 0.1×SSC, 0.1% SDS; and more specifically at 68° C., 0.1×SSC, 0.1% SDS). Hybridization requires that two nucleotides have complementary sequences, although mismatches between bases are possible depending on the severity of hybridization. The term "complementary" is used to describe the relationship between nucleotide bases that are capable of being hybridized with each other. For example, with respect to DNA, adenosine is complementary to thymine and cytosine is complementary to guanine. Therefore, the present disclosure may also include substantially similar nucleotide sequences as well as isolated polynucleotide fragments complementary to the entire sequence.

Specifically, the polynucleotide having homology can be detected using hybridization conditions including a hybridization step at a $T_m$ value of 55° C. and using the above-described conditions. In addition, the $T_m$ value may be 60° C., 63° C., or 65° C., but is not limited thereto. One of ordinary skill in the art can appropriately adjust the Tm value according to its purpose. The appropriate stringency of hybridizing the polynucleotides is dependent on the length and degree of complementarity of the polynucleotides, and the variables are well known in the art (see Sambrook et al., supra, 9.50-9.51, 11.7-11.8).

In particular, the expression "consist of the nucleotide sequence of SEQ ID NO: 1" means that, as when using a restriction enzyme, the addition, deletion, and/or mutation of a nucleotide is not excluded, which may occur during the process of linking to a target gene when the corresponding polynucleotide is ligated to the target gene and used as a promoter.

For example, the polynucleotide having the activity of a promoter consisting of the nucleotide sequence of SEQ ID NO: 1 can be included without limitation as long as it includes the nucleotide sequence which has the promoter activity of the present disclosure and which is hybridized under stringent conditions with a complementary sequence to all or a part of the nucleotide sequence of SEQ ID NO: 1.

Furthermore, the polynucleotide of the present disclosure may be operably linked to a gene encoding a target protein.

As used herein, the term "gene expression regulatory sequence" refers to a sequence which includes the polynucleotide of the present disclosure and is capable of expressing a target gene operably linked to the polynucleotide.

As used herein, the term "operably linked" means that the polynucleotide of the present disclosure having promoter activity is functionally linked to the gene sequence to initiate and mediate transcription of a target gene. Operable linking with the gene sequence can be achieved using a gene recombinant technique known in the art, and site-specific DNA cleavage and ligation can be performed by using a restriction enzyme and ligase known in the art, but these are not limited thereto.

Furthermore, the gene expression regulatory sequence of the present disclosure may further include any operator sequence for regulating transcription of genes other than promoters for performing the transcription of genes, as well as a sequence encoding a suitable mRNA ribosome binding site, DNA, etc. for regulating the termination of transcription and translation.

For example, a regulatory sequence suitable for prokaryotes may further include, in addition to promoters, ribosome binding sites, but is not limited thereto. The polynucleotide of the present disclosure having promoter activity may consist of a sequence for regulating the gene expression as described above, as required by one of ordinary skill in the art.

In the present disclosure, the target gene refers to a gene encoding a target protein whose expression is to be regulated in a microorganism.

For example, the gene may be a gene involved in the production of a product selected from the group consisting of amino acids (glutamic acid, etc.), organic acids (lactic acid, etc.), and combinations thereof, but is not limited thereto. Specifically, the gene may be a gene encoding an enzyme involved in the biosynthesis of amino acids (glutamic acid, etc.) and/or a gene encoding an enzyme involved in the biosynthesis of organic acids (lactic acid, etc.), but is not limited thereto. More specifically, the gene may be a gene encoding lactate dehydrogenase (LDH), but is not limited thereto. The sequence of the gene encoding the LDH can be easily obtained by one of ordinary skill in the art through a known database such as GenBank of the National Institutes of Health (NIH).

For example, the gene expression regulatory sequence of the present disclosure is operably linked to a gene sequence encoding LDH, and thus the production amount of glutamic acid in a microorganism may be increased and the production amount of lactic acid may be reduced.

Still another aspect of the present disclosure provides a vector comprising the gene; the polynucleotide; and a gene encoding a target protein operably linked to the polynucleotide.

The polynucleotide is as described above.

Specifically, the target protein may be lactate dehydrogenase (LDH).

As used herein, the term "vector" refers to an artificial DNA molecule having a genetic material capable of expressing a target gene in a suitable host, and refers to a DNA construct including the polynucleotide or a suitable gene expression regulatory sequence; and a nucleotide sequence of the gene encoding a target protein operably linked to the regulatory sequence.

The vector used in the present disclosure is not particularly limited as long as it can be expressed in a host cell, and any vector known in the art may be used to transform the host cell. Examples of the conventional vector may include natural or recombinant plasmids, cosmids, viruses, and bacteriophages.

For example, as a phage vector or cosmid vector, pWE15, M13, λLB3, λBL4, λIXII, λASHII, λAPII, λt10, λt11, Charon4A, Charon21A, etc. may be used; and as a plasmid vector, those based on pBR, pUC, pBluescriptII, pGEM, pTZ, pCL, pET, etc. may be used.

Additionally, an endogenous promoter in the chromosome may be replaced with the polynucleotide of the present disclosure having promoter activity via the vector for chromosomal insertion in the host cell. For example, vectors pECCG117, pDZ, pACYC177, pACYC184, pCL, pUC19, pBR322, pMW118, pCC1BAC, pCES208, pXMJ19, etc. may be used, but these are not limited thereto.

Additionally, the insertion of the polynucleotide into the chromosome may be accomplished by any method known in the art, e.g., by homologous recombination.

Since the vector of the present disclosure can be inserted into the chromosome by inducing a homologous recombination, the selection marker may be additionally included to confirm a successful gene insertion into the chromosome. A selection marker is for screening the cells which are transformed with the vector, in other words, for determining whether the polynucleotide is inserted. The markers that provide selectable phenotypes such as drug resistance, auxotrophy, resistance to toxic agents, or expression of surface proteins may be used. In an environment treated with a selective agent, only the cells expressing the selection marker can survive, or the cells show a different phenotype, and thus the successfully transformed cells can be selected through this method.

As used herein, the term "transformation" refers to the introduction of the vector comprising the polynucleotide or the gene expression regulatory sequence and the gene encoding a target protein into the host cell in order to allow the expression of the gene in the host cell. Furthermore, as long as the target gene can be expressed in the host cell, it does not matter whether the transformed polynucleotide and the gene encoding the target protein are located on the chromosome of the host cell or outside of the chromosome, and both cases are included.

The transformation method may include all methods of introducing the gene expression regulatory sequence and the gene encoding a target protein into the cell, and may be carried out by selecting a suitable standard technique known in the art depending on the host cell. For example, a suitable standard technique may be selected among electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, and a lithium acetate-DMSO technique, but is not limited thereto.

Still another aspect of the present disclosure provides a microorganism of the genus *Corynebacterium* comprising the polynucleotide; and a gene encoding a target gene operably linked to the polynucleotide.

The polynucleotide and gene encoding a target gene operably linked to the polynucleotide are as described above.

As used herein, the term "microorganism" includes all of a wild-type microorganism and a naturally or artificially genetically modified microorganism, and it may be a microorganism having a particular attenuated or reinforced mechanism due to insertion of a foreign gene or reinforcement or attenuation of activity of an endogenous gene.

In the present disclosure, the microorganism may include the polynucleotide, specifically the polynucleotide and/or a gene encoding a target gene operably linked to the polynucleotide. Alternatively, the microorganism may include the polynucleotide or the gene expression regulatory sequence and the vector including the polynucleotide or the gene expression regulatory sequence and the gene encoding a target protein, but is not limited thereto. In addition, the polynucleotide, the gene encoding the target protein, and the vector may be introduced into the microorganism by transformation, but are not limited thereto. Furthermore, as long as the gene can be expressed in the microorganism, it does not matter whether the polynucleotide and the gene encoding a target protein are located on the chromosome or outside of the chromosome.

For the objectives of the present disclosure, the microorganism including the polynucleotide and the gene encoding a target protein may be one in which the production amount of L-glutamic acid is increased and the production amount of lactic acid is reduced.

For example, the microorganism may have the polynucleotide in which the activity of lactate dehydrogenase is attenuated.

In the present disclosure, the microorganism may be included without limitation as long as it is a microorganism in which the polynucleotide of the present disclosure having promoter activity is introduced so that it operates as a promoter.

Specifically, the microorganism may be a microorganism of the genus *Corynebacterium*; more specifically may be *Corynebacterium glutamicum* or *Corynebacterium flavum*; and most specifically may be *Corynebacterium glutamicum*, but is not limited thereto.

Still another aspect of the present disclosure provides a method for producing a target substance, comprising: culturing the microorganism of the genus *Corynebacterium* in a medium; and recovering a target substance from the medium.

The polynucleotide and the microorganism are as described above.

In the present disclosure, the target substance may be an amino acid. Specifically, the amino acid may be an L-type amino acid unless otherwise stated, and may be an amino acid selected from the group consisting of glycine, alanine, valine, leucine, isoleucine, threonine, serine, cysteine, glutamine, methionine, aspartate, asparagine, glutamic acid, lysine, arginine, histidine, phenylalanine, tyrosine, tryptophan, proline, and a combination thereof, but is not limited thereto.

More specifically, the amino acid may be glutamic acid, but is not limited thereto.

As used herein, the term "culture" refers to culturing of a microorganism under artificially controlled environmental conditions. In the present disclosure, the method for producing a target substance using a microorganism with the polynucleotide may be carried out by a method widely known in the art. Specifically, the culture may be carried out in a batch process or in a continuous process such as a fed-batch process or a repeated fed-batch process, but is not limited thereto. The medium used for the culture must satisfy the requirements of a particular strain employed. The culture medium suitable for used in culturing the *Corynebacterium* strain is known in the art (e.g., Manual of Methods for General Bacteriology by the American Society for Bacteriology, Washington D.C., USA, 1981).

Carbon sources that can be used in the culture medium may be saccharides and carbohydrates such as glucose, sucrose, lactose, fructose, maltose, starch, and cellulose; oils and lipids such as soybean oil, sunflower seed oil, peanut oil, and coconut oil; fatty acids such as palmitic acid, steric acid, linoleic acid; alcohols such as glycerol and ethanol; and organic acids such as acetic acid. These materials may be used separately or in combination, but are not limited thereto.

Examples of nitrogen sources that can be used include peptone, yeast extract, broth, malt extract, corn steep liquor, soybean meal and urea, or inorganic compounds such as ammonium sulfate, ammonium chloride, ammonium phosphate, ammonium carbonate, and ammonium nitrate. These nitrogen sources may also be used separately or in combination, but are not limited thereto.

Phosphorous sources that can be used in the culture medium may include dipotassium hydrogen phosphate, potassium dihydrogen phosphate, or corresponding sodium-containing salts. In addition, the culture medium may contain metal salts essential to the growth of cells, and may be supplemented with materials essential for the growth, such as amino acids and vitamins in addition to the materials above. Further, precursors suitable for the culture medium may be used. The above raw substances may be adequately fed into the culture in a batch or continuous manner.

During the culture of the microorganism, the pH of the culture may be adjusted by a proper basic compound such as sodium hydroxide, potassium hydroxide, or ammonia, or an acidic compound such as phosphoric acid or sulfuric acid. Foaming may be adjusted by an anti-foaming agent such as a fatty acid polyglycol ester. The aerobic condition of the culture may be maintained by introducing oxygen or oxygen-containing gas mixtures (e.g., air).

The temperature of the culture (medium) may be generally 20° C. to 45° C., specifically 25° C. to 40° C. Culturing may be continued until the desired production amount of the target substance is obtained, specifically for 10 hours to 160 hours.

The recovery of the target substance from the culture (medium) may be carried out by a conventional separation method known in the art. For the separation method, methods such as centrifugation, filtration, chromatography, crystallization, etc. may be used. For example, a supernatant obtained by centrifuging the culture medium at a low speed to remove biomass may be separated by ion-exchange chromatography, but is not limited thereto. In an alternative method, the target substance may be recovered without an additional purification process, by performing processes of separation of bacterial cells from a culture product (medium) and filtration. In another alternative method, the target substance may be recovered, and the recovery step may further include a purification process.

Still another aspect of the present disclosure provides a method for preparing a fermented composition, comprising fermenting by culturing the microorganism of the genus *Corynebacterium* in a medium.

Still another aspect of the present disclosure provides a fermented composition prepared by the above method.

The polynucleotide and microorganism are as described above, and the step of culturing the microorganism in a medium is also as described above.

As used herein, the term "the fermented composition" refers to a composition obtained by culturing the microorganism of the present disclosure in a medium. Furthermore, the fermentation composition may include a composition in the form of a liquid or powder obtained after culturing the microorganism followed by a suitable post-treatment. In particular, the suitable post-treatment process may include, for example, a process of culturing a microorganism, a process of removing bacterial cells, a concentration process, a filtration process, and a process of mixing carriers, and may further include a drying process. In some cases, the post-treatment process may not include a purification process. The fermentation composition, obtained by culturing the microorganism of the present disclosure, is characterized in that the amount of glutamic acid production is increased while the amount of lactic acid production is reduced, thereby making it possible to provide an optimum taste.

Additionally, "the fermentation composition" does not exclude seasoning products (e.g., powdered soup products, snack seasoning products, etc.) containing the composition in the form of a liquid or powder. Furthermore, "the fermentation composition" does not exclude cases in which a substance obtained by a non-fermentation process or another substance obtained by a non-natural process is further included, as long as the composition obtained by culturing the microorganism of the present disclosure is contained therein.

Advantageous Effect

The novel promoter of the present disclosure can be introduced into a microorganism producing amino acids, thereby increasing the production amount of the amino acids in the microorganism and decreasing the production amount of organic acids. Specifically, when L-glutamic acid is prepared using the novel promoter of the present disclosure, the amounts of L-glutamic acid and organic acids in a fermented product are adjusted to improve the taste and palatability of the fermented product.

DETAILED DESCRIPTION OF THE EMBODIMENT

Hereinbelow, the present disclosure will be described in detail with accompanying exemplary embodiments. However, the exemplary embodiments disclosed herein are only for illustrative purposes and should not be construed as limiting the scope of the present disclosure.

Example 1

Selection of Mutant Strain for Reducing Lactic Acid Productivity

Example 1-1

Induction of Random Mutation by UV Irradiation

In order to select mutant strains in which the productivity of L-glutamic acid, which is a target product of fermentation, is improved and in which the productivity of lactic acid, which reduces the palatability of a fermented product, is decreased, wild-type *Corynebacterium glutamicum* (ATCC13869) was plated on nutrient media containing agar and cultured at 30° C. for 16 hours. Hundreds of the thus-obtained colonies were irradiated with UV at room temperature to induce a random mutation on the genome in the strain.

Example 1-2

Experiment on Fermentation Titer of Mutation-Inducting Strain and Selection of Strain Thereafter, the experiment on fermentation titer of the mutant strains, in which the random mutation had been induced, was carried out.

Each colony was subcultured in the nutrient media, and then cultured in fermentation media for 5 hours. Thereafter, 25% tween 40 was added to each medium at a concentration of 0.4%, and then each colony was cultured again for 32 hours.

Nutrient Medium

Glucose 1%, meat juice 0.5%, polypeptone 1%, sodium chloride 0.25%, yeast extract 0.5%, agar 2%, urea 0.2%, pH 7.2

Fermentation Medium

Raw sugar 6%, calcium carbonate 5%, ammonium sulfate 2.25%, potassium monophosphate 0.1%, magnesium sulfate 0.04%, iron sulfate (10 mg/L), biotin (0.3 mg/L), thiamine hydrochloride (0.2 mg/L)

Each of the colonies was cultured under the conditions above, and then mutant strains producing L-glutamic acid, the produced amount of which is equal to or greater than that produced by wild-type *Corynebacterium glutamicum* (ATCC13869), were selected. In addition, with respect to the selected mutant strains, the concentration of L-glutamic acid was measured by YSI, and the concentration of lactic acid was measured by HPLC. The measured concentrations of L-glutamic acid and lactic acid are shown in Table 1.

TABLE 1

| Strain | L-Glutamic acid (g/L) | Lactic acid (g/L) |
| --- | --- | --- |
| ATCC13869 | 14.5 | 1.5 |
| ATCC13869-m1 | 15.1 | 1.2 |
| ATCC13869-m2 | 14.0 | 0.7 |
| ATCC13869-m3 | 17.7 | 1.5 |
| ATCC13869-m4 | 13.9 | 2.0 |
| ATCC13869-m5 | 14.4 | 1.8 |
| ATCC13869-m6 | 16.7 | 0.9 |
| ATCC13869-m7 | 18.8 | 0.4 |
| ATCC13869-m8 | 16.2 | 0.7 |
| ATCC13869-m9 | 18.9 | 0.1 |
| ATCC13869-m10 | 12.4 | 2.1 |
| ATCC13869-m11 | 13.8 | 2.1 |
| ATCC13869-m12 | 15.7 | 1.4 |
| ATCC13869-m13 | 15.3 | 0.8 |
| ATCC13869-m14 | 16.4 | 1.0 |
| ATCC13869-m15 | 17.2 | 1.1 |
| ATCC13869-m16 | 18.2 | 0.7 |

Based on Table 1, "ATCC13869-m7" and "ATCC13869-m9" were selected as the strains in which the amount of L-glutamic acid produced was increased and the amount of lactic acid produced was decreased compared to those produced in the wild-type strain.

Example 2

Confirmation of Mutation Through Gene Sequencing

In order to confirm the gene mutation of the mutant strains, genes in the strains ATCC13869-m7 and ATCC13869-m9 were compared with those of the wild-type strain.

As a result, it was found that the strains ATCC13869-m7 and ATCC13869-m9 contained the same mutation at a specific position in the promoter region of a gene encoding lactate dehydrogenase.

Specifically, it was confirmed that ATCC13869-m7 and ATCC13869-m9 contained a mutation in which the $37^{th}$ nucleotide, T, in the sequence of the promoter region of SEQ ID NO: 2 is substituted with G. It was confirmed that the promoter region of SEQ ID NO: 2 was a sequence commonly included in a microorganism of the genus *Corynebacterium*, more specifically, the wild-type *Corynebacterium glutamicum* (ATCC13032, ATCC13869, and ATCC14067).

Therefore, in Examples 3 and 4, attempts were made to confirm whether the mutation above affected the production amounts of glutamic acid and lactic acid in the microorganism of the genus *Corynebacterium*.

Example 3

Preparation of Strain Introduced with Mutation and Confirmation of Production Amount of Lactic Acid Example 3-1

Preparation of Strain Introduced with Mutation

An attempt was made to prepare a mutant strain introduced with the mutation confirmed in Example 2. Specifically, in order to introduce the mutation into the wild-type *Corynebacterium glutamicum* ATCC13869 and ATCC13032 (i.e., in order to substitute the $37^{th}$ nucleotide of the polynucleotide sequence of SEQ ID NO: 2 with G), the oligonucleotide in a reverse direction, which contains a target mutation, was designed with a 75-mer length.

Specifically, the oligonucleotide (30 μg) of SEQ ID NO: 5 was transformed into the wild-type *Corynebacterium glutamicum* strains ATCC13869 and ATCC13032 using an electric pulse method (Appl. Microbiol. Biotechnol., 1999, 52:541-545), and then a complex liquid medium (1 mL) was added thereto. The resultants were then cultured at 30° C. for 30 minutes while shaking at 160 rpm. Thereafter, the culture medium was incubated on ice for 10 minutes, centrifuged at 4000 rpm at 4° C. for 10 minutes, and then the supernatant was removed to obtain microbial cells. Thereafter, 1 mL of a 10% glycerol solution (4° C.) was added thereto and mixed, and then the resultants were centrifuged at 4000 rpm at 4° C. for 10 minutes. The supernatant was removed and then the microbial cells were washed. Such procedure was repeated once more to wash the microbial cells again, and a 10% glycerol solution (4° C. and 0.1 mL) was added thereto to prepare the strains for the next transformation. Thereafter, the process for the transformation was repeated 10 times with the oligonucleotide of SEQ ID NO: 5 using the electric pulse method described above, and then the resultants were plated on a complex plate medium to obtain colonies (Nat. Protoc., 2014 October; 9(10): 2301-16).

As a result of carrying out the analysis of the gene sequence of the obtained colonies, it was confirmed that the target mutation was introduced into the strains. In addition, the strains into which the mutation was introduced were named as "ATCC13869::ldh-pro-1mt" and "ATCC13032::ldh-pro-1mt".

Example 3-2

Confirmation of Production Amount of Lactic Acid

The mutant strains ATCC13869::ldh-pro-1mt and ATCC13032::ldh-pro-1mt, which were prepared in Example 3-1, and their wild-type *Corynebacterium glutamicum* strains ATCC13869 and ATCC13032 were cultured in the same manner as in Example 1-2.

After the cultivation was completed, the concentrations of L-glutamic acid and lactic acid in each medium were measured. The measured concentrations of L-glutamic acid and lactic acid are shown in Table 2 below.

TABLE 2

| Strain | L-Glutamic acid (g/L) | Lactic acid (g/L) |
|---|---|---|
| ATCC13869 | 14.5 | 1.5 |
| ATCC13869::ldh-pro-1mt | 19.2 | 0.0 |
| ATCC13032 | 8.2 | 2.7 |
| ATCC13032::ldh-pro-1mt | 10.8 | 0.3 |

As shown in Table 2, it was confirmed that the concentration of L-glutamic acid produced by the *Corynebacterium glutamicum* strain ATCC13869::ldh-pro-1mt, into which the mutation was introduced, was higher than that produced by the wild-type *Corynebacterium glutamicum* strain ATCC13869 by about 4.7 g/L (about 32%). On the other hand, the wild-type *Corynebacterium glutamicum* strain ATCC13869 produced 1.5 g/L of lactic acid, but lactic acid was not measured in the medium in which the strain ATCC13869::ldh-pro-1mt was cultured.

Additionally, it was confirmed that the concentration of L-glutamic acid produced by the *Corynebacterium glutamicum* strain ATCC13032::ldh-pro-1mt, into which the mutation was introduced, was higher than that produced by the wild-type *Corynebacterium glutamicum* strain ATCC13032 by about 2.6 g/L (about 32%). On the other hand, the wild-type *Corynebacterium glutamicum* strain ATCC13032 produced 2.7 g/L of lactic acid, but a trace amount of lactic acid (0.3 g/L) was measured in the medium in which the strain ATCC13032::ldh-pro-1mt was cultured.

That is, it was confirmed that the mutation increased the L-glutamic acid productivity and reduced the lactic acid productivity in the microorganisms.

Additionally, the strain ATCC13869::ldh-pro-1mt was named as CA02-9209 and deposited at the Korean Culture Center of Microorganisms (KCCM), which is an international depositary authority under the Budapest Treaty, on Feb. 28, 2018, and was assigned Accession No. KCCM12227P.

Example 4

Confirmation of Enzyme Activity and Amount of Lactic Acid Produced in strain KFCC11074 into which mutation is introduced Example 4-1

Preparation of Vector in to which Mutation is Introduced

In order to confirm whether the mutation exhibits the same effect in the strains with improved productivity of glutamic acid, in addition to the wild-type strains, attempts were made to introduce the mutation into the strain KFCC11074 (Korean Patent No. 10-0292299), which is known as a glutamic acid-producing strain.

Specifically, a vector for gene substitution was constructed in order to substitute the $37^{th}$ nucleotide of the polynucleotide sequence of SEQ ID NO: 2, which is contained in the strain, with G. The gene fragments for constructing the vector were obtained by PCR using ATCC13869 genomic DNA as a template. Based on information on genes and adjacent sequences of the *Corynebacterium glutamicum* (ATCC13869) registered in the National Institutes of Health GenBank (NIH GenBank), primers including the polynucleotides of SEQ ID NOS: 6, 7, 8, and 9 were prepared.

After denaturation at 95° C. for 5 minutes, PCR was carried out for a total of 30 cycles under the following conditions: denaturation at 95° C. for 20 seconds, annealing at 55° C. for 20 seconds, and polymerization at 72° C. for 30 seconds. Thereafter, the polymerization reaction was carried out at 72° C. for 5 minutes. More specifically, the polynucleotide (500 bp) amplified using the primers of SEQ ID NOS: 6 and 7 and the polynucleotide (500 bp) amplified using the primers of SEQ ID NOS: 8 and 9 were obtained. The obtained two DNA fragments were ligated to the vector pDZ (Korean Patent No. 10-0924065 and International Publication No. 2008-033001), which had been digested with restriction enzymes BamHI and SalI, by using an infusion enzyme, and thereby a vector for gene substitution was prepared. The prepared vector was named as "pDZ-ldh-pro-1mt". The information on the primer sequences used for the vector preparation is shown in Table 3 below.

TABLE 3

| SEQ ID NO: | Primer | Sequence (5' to 3') |
|---|---|---|
| 6 | ldh-pro-1mt-AF | CGGTACCCGGGGATCCTGTGGGTGGCGTTGTA |
| 7 | ldh-pro-1mt-AR | CTTTGTTACACCTTTACTTATGCCCGATTATGT |
| 8 | ldh-pro-1mt-BF | GTAAAGGTGTAACAAAGGAATCCGGGCACAAGC |
| 9 | ldh-pro-1mt-BR | ATGCCTGCAGGTCGACCCACACTGCGTAGGTC |

Example 4-2

Preparation of KFCC11074 into which mutation is introduced and confirmation of production amount of lactic acid The vector for gene substitution, which had been prepared in Example 4-1, was introduced into the strain KFCC11074 to prepare "KFCC11074::ldh-pro-1mt", which is the glutamic acid-producing strain into which the mutation is introduced. The *Corynebacterium glutamicum* strain KFCC11074, into which the mutation was not introduced, and the strain KFCC11074::ldh-pro-1mt were each cultured in the same manner as in Example 1-2.

After completion of the culture, the concentrations of L-glutamic acid and lactic acid in each medium were measured. The measured concentrations of L-glutamic acid and lactic acid are shown in Table 4 below.

TABLE 4

| Strain | L-Glutamic acid (g/L) | L-Lactic acid (g/L) |
|---|---|---|
| KFCC11074 | 9.1 | 22.5 |
| KFCC11074::ldh-pro-1mt | 17.1 | 6.5 |

As shown in Table 4, it was confirmed that the concentration of L-glutamic acid produced by the *Corynebacterium glutamicum* strain KFCC11074::ldh-pro-1mt, into which the mutation is introduced, was higher than that produced by the *Corynebacterium glutamicum* strain KFCC11074, into which the mutation is not introduced, by about 8 g/L (about 88%).

On the other hand, it was confirmed that the concentration of lactic acid produced by the strain KFCC11074::ldh-pro-1mt was lower than that produced by the *Corynebacterium glutamicum* strain KFCC11074, into which the mutation is not introduced, by 17 g/L.

That is, it was once again confirmed that the mutation increased the L-glutamic acid productivity in the microorganisms and decreased the lactic acid productivity.

Example 4-3

Confirmation of Activity of Enzyme LDH of KFCC11074 into which Mutation is Introduced Since the mechanism for the reduction of the lactic acid productivity in the strain KFCC11074::ldh-pro-1mt, which had been prepared in Example 4-2, was confirmed, and since it was confirmed that the mutation was contained in the promoter of lactate dehydrogenase (LDH), attempts were made to identify the activity of lactate dehydrogenase, which is a lactic acid-producing enzyme, depending on the mutation.

Specifically, the activity of the enzyme was evaluated in the following manner. First, cells were cultured in medium #3 (25 mL), which has the composition below, in a flask (250 mL) at 200 rpm at 30° C. for 6 hours. Thereafter, the supernatant was removed by precipitating the cells at 4000 rpm for 10 minutes, and cell washing was repeated three times using 20 mM Tris-HCl (25 mL, pH 7.5). After washing, the supernatant was removed, and the cells were resuspended using 15% glycerol buffer (2 mL) in 20 mM Tris (pH 7.5) for cell extraction. The resuspended cells (1 mL) were placed in a bead tube and homogenized six times under a condition of 46/30 seconds using a homogenizer. Thereafter, the resultants were centrifuged at 13000 rpm at 4° C. for 20 minutes.

Medium #3:

Glucose 2%, polypeptone 1%, $(NH_4)_2SO_4$ 1%, $KH_2PO_4$ 0.52%, $K_2HPO_4$ 1.07%, yeast extract 1%, urea 0.15%, $MgSO_4 \cdot 7H_2O$ 0.05%, d-biotin (1.8 mg/L), thiamin-HCl (9 mg/L), calcium-pantothenic acid (9 mg/L), niacinamide (60 mg/L)

Thereafter, the Bradford assay was carried out to confirm and standardize the concentration of protein contained in the supernatant (sample) obtained from the bead tube. The Bradford assay obtained a standard curve with reference to Tables 5 and 6 below and confirmed the concentration of the sample. In particular, the 1× Biorad protein assay reagent (980 μL) was added to the sample having a total volume of 20 μL and then vortexed to measure the absorbance at 595 nm for about 3 minutes.

TABLE 5

STD and Extract Sampling

| mg/mL | 0 | 0.025 | 0.05 | 0.1 | 0.2 |
|---|---|---|---|---|---|
| BSA (1 mg/mL) (μL) | 0 | 0.5 | 1 | 2 | 4 |
| Extraction buffer (μL) | 20 | 19.5 | 19 | 18 | 16 |
| Total volume (μL) | 20 | 20 | 20 | 20 | 20 |

TABLE 6

| Cell extract | 1:10 dilution | 1:5 dilution | 1:20 dilution | 1:50 dilution |
|---|---|---|---|---|
| Cell extract (μL) | 2 | 4 | (1/10)10 | (1/10)4 |
| Extraction buffer (μL) | 18 | 16 | 10 | 16 |
| Total volume (μL) | 20 | 20 | 20 | 20 |

Thereafter, the experiment on the activities of lactate dehydrogenases in the strains KFCC11074 and KFCC11074::ldh-pro-1mt was carried out using the reaction solution, the composition ratio of which is shown in Table 7 below. Further, 30 mM sodium pyruvate was used as a starter. Furthermore, the activities of lactate dehydrogenase in the two strains, which were measured under the conditions shown in Table 8, are shown in Table 9 below.

TABLE 7

| Reaction solution | Per 1 reaction |
|---|---|
| 0.2M Tris-HCl pH 7.5 (μL) | 500 |
| 30 mM Sodium pyruvate (μL) | 100 |
| 6.6 mM NADH (μL) | 50 |
| Cell extract (mg/mL) | 178 μg |
| DDW | Up to 1 mL |

TABLE 8

| Cuvette | 10 mm | |
|---|---|---|
| Wavelength | 340 | nm |
| Unit | U | |
| Factor | −1 | |
| Decimal places | 3 | |
| Temperature on | on | |
| Temperature | 25 | ° C. |
| Measuring Procedure | lin. regr. | |
| Delay | 00:01 | min:sec |
| Measuring time | 1:30 | min:sec |
| Interval | 00:8 | min:sec |
| Autoprint | off | |

TABLE 9

| Strain | LDH activity (U) |
|---|---|
| KFCC11074 | 0.398 |
| KFCC11074::ldh-pro-1mt | 0.150 |

As shown in Table 9, it was confirmed that the activity of lactate dehydrogenase was reduced in the strains into which the mutation is introduced.

That is, it was confirmed that the mutation reduced the activity of lactate dehydrogenase in the microorganisms, thereby reducing the lactic acid productivity.

In summary, the polynucleotide of the present disclosure is a promoter of lactate dehydrogenase including the mutation in which a single nucleotide is substituted, and thus the polynucleotide can attenuate the activity of lactate dehydrogenase in the wild-type strains or the glutamic acid-producing strains via the activity of the mutated promoter; as a result, the productivity of glutamic acid, which is a target product of fermentation, is increased, and further, the productivity of lactic acid, which lowers the palatability of the fermented product, is reduced. Accordingly, the polynucleotide of the present disclosure can be effectively used in various industrial fields for producing glutamic acid at a high yield.

From the foregoing, one of ordinary skill in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

Accession Number

Depository Institution: Korean Culture Center of Microorganisms (International Depositary Authority)
Accession Number: KCCM12227P
Date of Deposit: Feb. 28, 2018

The invention claimed is:

1. A polynucleotide comprising a nucleotide sequence having promoter activity, wherein the nucleotide sequence having promoter activity consists of SEQ ID NO: 1.

2. The polynucleotide according to claim 1, wherein the nucleotide sequence having promoter activity is operably linked to a gene encoding a target protein.

3. A vector comprising the polynucleotide of claim 1, wherein a gene encoding a target protein is operably linked to the nucleotide sequence having promoter activity.

4. The vector of claim 3, wherein the target protein is lactate dehydrogenase.

5. A microorganism of the genus *Corynebacterium*, comprising the polynucleotide of claim 1; wherein a gene encoding a target protein is operably linked to the nucleotide sequence having promoter activity.

6. The microorganism according to claim 5, wherein the target protein is lactate dehydrogenase.

7. The microorganism according to claim 5, wherein the microorganism of the genus *Corynebacterium* is *Corynebacterium glutamicum*.

8. A method for producing a target substance, comprising:
    culturing the microorganism of the genus *Corynebacterium* of claim 5 in a medium; and
    recovering the target substance from the cultured medium.

9. The method according to claim 8, wherein the target substance is an amino acid.

10. A method for preparing a fermented composition, comprising fermenting by culturing the microorganism of the genus *Corynebacterium* of claim 5 in a medium.

11. The microorganism according to claim 7, wherein the target protein is lactate dehydrogenase.

12. The method of claim 8, wherein the target protein is lactate dehydrogenase.

* * * * *